(12) United States Patent
Padgett

(10) Patent No.: US 8,198,057 B2
(45) Date of Patent: Jun. 12, 2012

(54) ETHANOL PRODUCTION BY FERMENTATION OF CHINESE TALLOW TREE

(75) Inventor: Randall Padgett, Panama City, FL (US)

(73) Assignee: Alternative Green Technologies, LLC, Panama City, FL (US)

( * ) Notice: Subject to any disclaimer, the term of this patent is extended or adjusted under 35 U.S.C. 154(b) by 285 days.

(21) Appl. No.: 12/480,503

(22) Filed: Jun. 8, 2009

(65) Prior Publication Data

US 2010/0311138 A1  Dec. 9, 2010

(51) Int. Cl.
*C12P 7/06* (2006.01)
(52) U.S. Cl. .................................................. 435/161
(58) Field of Classification Search ................ None
See application file for complete search history.

(56) References Cited

U.S. PATENT DOCUMENTS

| | | | |
|---|---|---|---|
| 3,871,961 A | 3/1975 | Gianessi | |
| 4,178,154 A | 12/1979 | Rothlisberger | |
| 4,278,471 A | 7/1981 | Whittingham | |
| 4,368,056 A | 1/1983 | Pierce et al. | |
| 4,564,595 A | 1/1986 | Neves | |
| 4,612,286 A | 9/1986 | Sherman et al. | |
| 4,787,939 A | 11/1988 | Barker et al. | |
| 5,047,332 A | 9/1991 | Chahal | |
| 5,053,231 A | 10/1991 | Riffkin et al. | |
| 5,352,593 A * | 10/1994 | Earl | 435/161 |
| 5,482,846 A | 1/1996 | Ingram et al. | |
| 5,865,898 A | 2/1999 | Holtzapple et al. | |
| 6,102,690 A | 8/2000 | Ingram et al. | |
| 6,333,181 B1 | 12/2001 | Ingram et al. | |
| 7,091,014 B1 | 8/2006 | Aristidou et al. | |
| 7,101,691 B2 | 9/2006 | Kinley et al. | |
| 7,223,402 B2 | 5/2007 | Cheung | |
| 7,468,263 B2 | 12/2008 | Kishida et al. | |
| 2008/0006536 A1 | 1/2008 | Cuomo et al. | |
| 2008/0182309 A1* | 7/2008 | Vlad | 435/161 |
| 2008/0190013 A1 | 8/2008 | Argyropoulos | |
| 2008/0193595 A1* | 8/2008 | De Vuyst et al. | 426/45 |
| 2009/0117633 A1 | 5/2009 | Bradley | |
| 2009/0117634 A1 | 5/2009 | Bradley | |

FOREIGN PATENT DOCUMENTS

WO  PCT/SE2004/001786  6/2005

OTHER PUBLICATIONS

Meier et al., Helvetica Physiologica et Pharmacologica ACTA, 1956, vol. 14, No. 3, pp. 279-288.*
Meier et al., Helvetica Physiologica et Pharmacologica ACTA, 1956.*
Paul A. Olivier Ph.D., From Field to Factory to Diesel Tank, Empowering Louisiana Agriculture, A New Cash Crop.
Thomas L. Eberhardt et al., Chinese Tallow Tree (*Sapium sebiferum*) Utilization: Characterization of Extractives and Cell-Wall Chemistry, Wood and Fiber Science, 39(2), 2007, pp. 319-324, Society of Wood Science and Technology.
USDA, NRCS, National Plant Data Center & Louisiana State Univeristy—Plant Science, Exotic Weed Species, Chinese Tallow Tree *Triadica sebifera* (L.) Small, www.hear.org/pier/pdf/nrcs$_{13}$ plant_guide_triadica_sebifera.pdf.
Peter Fairley, Can Magnets Boost Ethanol Production?, www.technologyreview.com/Energy/19412/?a=f, Sep. 21, 2007, Technology Review, MIT.
B.E. Wood et al., Ultrasound stimulates ethanol production during the simultaneous saccharification and fermentation of mixed waste office paper, Biotechnology progress 1997; 13(3):232-7, www.biomedexperts.com/Abstract.bme/9190074/ultrasound_stimulates_ethanol_production_during_the_simultaneous_saccharification_and_fermentation_of_mixed_waste_office.
Kevin Bullis, Making Ethanol from Wood Chips, www.technologyreview.com/energy/17799/?a=f, Nov. 16, 2006, Technology Review, MIT.
Ethanol Fermentation of Mahula (*Madhuca latifolia* L) . . . , Swain, M.R. et al., Microbiological Research, Apr. 2007, vol. 162, p. 93-98.
The Weedy Truth about Biofuels, Low, T. et al., Invasive Species Council, Oct. 2007.
International Search and Opinion for PCT/US2010/037529.

* cited by examiner

*Primary Examiner* — Allison Ford
*Assistant Examiner* — Yvonne Pyla
(74) *Attorney, Agent, or Firm* — Mark Swanson; Bradley Arant Boult Cummings

(57) ABSTRACT

A method for producing ethanol by fermentation includes the preparation of a starter culture, inoculation of a mash with the starter culture, fermentation of the mash, and recovery of ethanol from the mash. The starter culture includes a tallow base with Chinese tallow tree parts and water which are inoculated with micro-organisms, where the micro-organisms include yeast. The micro-organisms are grown in the tallow base, and used to inoculate the mash. The mash is then fermented, and ethanol is recovered from the mash.

9 Claims, 1 Drawing Sheet

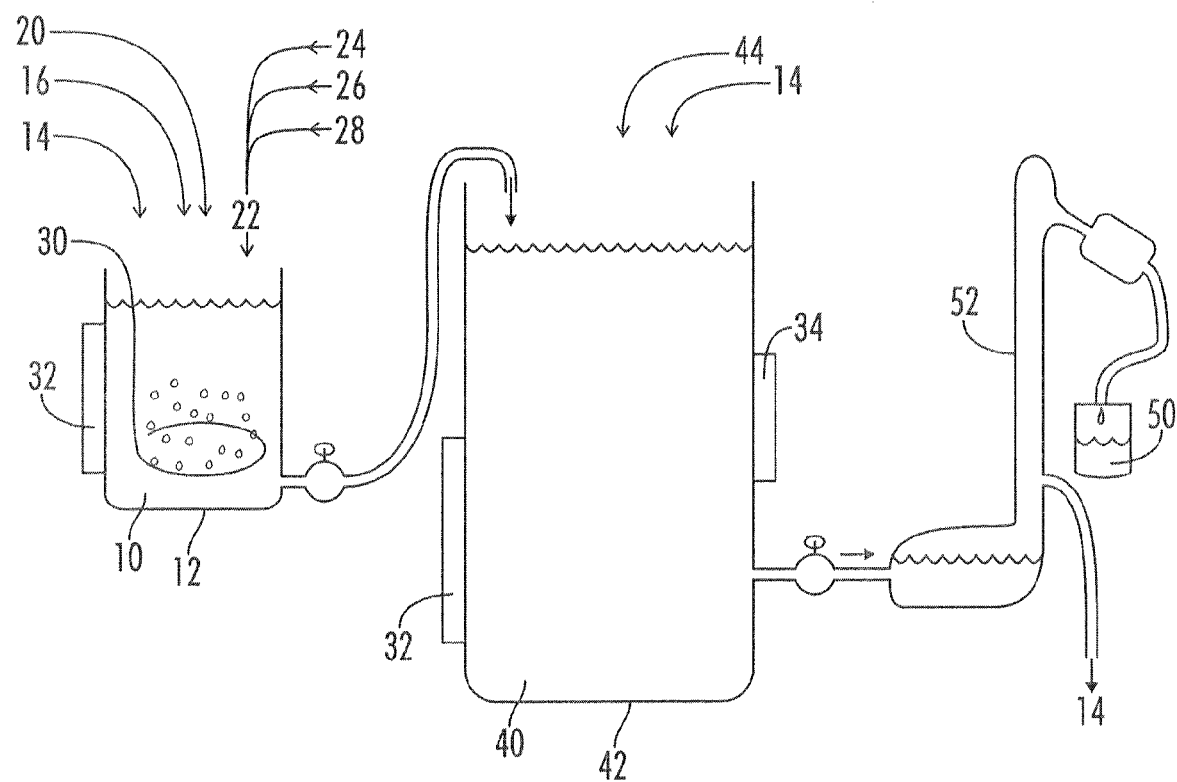

ETHANOL PRODUCTION BY FERMENTATION OF CHINESE TALLOW TREE

BACKGROUND OF THE INVENTION a. Field of the Invention

This invention relates to methods for converting organic materials into ethanol.

b. Background of the Invention

Ethanol is a chemical compound having the formula $C_2OH6$. Ethanol includes two carbons connected to a hydroxyl unit. Ethanol is flammable with a flash point of approximately 13° C. and a boiling point of approximately 78° C. It is completely miscible with water. It is a volatile, colorless liquid with a strong order, and it tends to burn with a smokeless blue flame which is not always visible in normal light. Ethanol has a characteristic azeotrope with water. When mixtures of ethanol and water are distilled at atmospheric pressure, the maximum concentration of ethanol in the overhead distillate is approximately 96% by volume, with the remaining 4% by volume of the overhead distillate being water. Ethanol has a specific gravity of approximately 0.789 grams per cubic centimeter, and a chemical abstract services, or CAS number of 64-17-5.

When pure ethanol is mixed with pure water, the resulting solution has less volume than the two components. So if one liter of pure ethanol was mixed with one liter of pure water, the resulting mixture would have a volume of less than two liters. The mixture is also exothermic and will give off heat, so when pure ethanol is mixed with water the resulting solution will be warmer than the combination of just the ethanol and the water. Ethanol is the alcohol that is commonly consumed in beverages such as beer, wine and liquor and is responsible for the intoxicating effects of alcohol on people.

There are many uses for ethanol. For example, ethanol has many advantageous properties when used as a solvent. It has a polar end and a non-polar end such that many compounds will be soluble in ethanol, where the more polar compounds are attracted to the hydroxyl (OH) group attached to the ethanol, and the non-polar compounds are attracted to the ethyl group on the opposite end of the molecule. Ethanol can be used as a raw material in the production of many compounds. These compounds include ethyl halides, diethyl ether, ethyl esters, butadiene, acetic acid, and ethylamines, amongst others. Ethanol is also used as an antiseptic, and can be included in medical wipes and in certain antibacterial hand sanitizer gels. Ethanol tends to kill organisms by denaturing their proteins and dissolving their liquids, and it is effective against many bacteria, fungi and also many viruses. It can be used as a food source, although it is intoxicating Ethanol can also be used as fuel. It has been used as rocket fuel in certain early bio-propellant rocket vehicles, where it was used in conjunction with an oxidizer. It can be used with ethanol fuel cells to produce electricity. It can also be used as a fuel for combustion in automobiles. Varying concentrations of ethanol are used as fuel for automobiles and other vehicles. Many fuels available in the United States include ethanol at concentrations up to 10%. There are also E85 cars which can burn ethanol at concentrations of 85%, with the remaining 15% being a petroleum based fuel. The E85 fuels tend to store less energy per liter than petroleum based fuels, such as gasoline. Therefore, the efficiency in miles per gallon of a vehicle using 85% ethanol will typically be less than for a comparable vehicle using pure gasoline.

Ethanol is frequently produced industrially by fermentation processes. For example, a source of organic material, such as a food source, can be inoculated with yeast. The yeast will then begin to consume the organic material, and give off ethanol as a metabolic waste product. There are other micro-organisms that can be used in place of yeast for fermentation. These other micro-organisms include *Zymomonas Mobilis* and *Escherichia Coli*, as well as others. Ethanol produced by micro-organisms tends to be toxic to the micro-organisms, so when ethanol is produced above certain levels it inhibits the micro-organisms and stops the fermentation process. Micro-organisms are more efficient at converting some sorts of organic compounds than others. The commonly used baker's yeast tends to be more efficient at converting sugars in such things as sugar cane or corn than in converting cellulosic materials into ethanol. Most ethanol production in the world now is based on organic materials with high sugar content, such as corn or sugar cane.

There have been many attempts to come up with efficient methods for efficiently converting cellulosic materials to ethanol, and these have met with varied success. Many times the use of cellulosic feed sources will involve some sort of pre-treatment technique to make the cellulose available to the micro-organisms. This can include acid hydrolysis, steam explosion, ammonia expansion, alkaline wet oxidation or ozone pre-treatment, amongst others. It is also possible to produce ethanol by means other than fermentation, such as gasification.

After the fermentation process, the ethanol is typically recovered from the fermentation mash. This is frequently done through distillation, and the ethanol is recovered with water as an azeotrope. There are other techniques of recovering ethanol from a fermentation mash which could be used. There are also ways to recover pure ethanol from an azeotropic mixture of water and ethanol. For example, the collected overhead ethanol and water can be run through a carbon absorption system to absorb the water, leaving essentially pure ethanol.

In the fermentation process, carbon dioxide is generated as a by-product, and this carbon dioxide typically bubbles out of the fermentation mash. The fermentation of an organic material with microorganisms is typically done anaerobically, or not in the presence of oxygen. When little or no oxygen is present, the micro-organisms find energy from the food source and not from available free oxygen. Many micro-organisms, including some yeasts, will utilize different mechanisms for consuming organic materials in anaerobic vs. aerobic conditions. Some yeast will preferentially produce water instead of ethanol as a by-product of metabolism when oxygen is present.

SUMMARY OF THE INVENTION

The invention includes two primary components which can be used separately, or in combination. The first component is the preparation of a starter culture, and the second component is fermentation and recovery of ethanol. The starter culture is prepared by inoculating a tallow base with micro-organisms, where the micro-organisms include yeast. The tallow base includes Chinese tallow tree parts and water. The micro-organisms are then grown in the tallow base to produce the starter culture. The fermentation component includes providing a mash which includes an organic material and water. The mash is inoculated with a micro-organism, such as in the starter culture, and the mash is fermented. Ethanol is recovered from the mash.

BRIEF DESCRIPTION OF THE DRAWINGS

The attached FIGURE is a schematic drawing of an ethanol production system.

DETAILED DESCRIPTION

The current description describes a process for producing ethanol which includes 1) the preparation of a starter culture 10, 2) the fermentation of a mash, and 3) recovery of the ethanol, as seen in the attached FIGURE.

Starter Culture

Micro-organisms are adapted in the starter culture preparation to more efficiently produce ethanol from a wide variety of organic materials. The micro-organisms are adapted as opposed to being acclimated. The term "adaptation" as used in this description involves modifying the environment of the micro-organisms such that the micro-organisms develop the ability to live and thrive in conditions which are different than the conditions in the environment in which the micro-organisms were adapted. If the fermentation mash had the same conditions as the starter culture, the micro-organisms would be acclimated, as opposed to adapted. "Acclamation" refers to exposing the micro-organisms to an environment the same as that in which they will function, so that they will develop the ability to function more effectively in that one particular environment.

Tallow Base

A method has been developed which produces a starter culture 10 including micro-organisms 22 which are able to ferment a wide variety of organic materials 44. The organic materials 44 fermented vary from the organic materials 44 used in the starter culture 10 where the micro-organisms 22 are adapted. A starter culture vessel 12 is used for the preparation of the starter culture 10. Water 14 and various parts of a Chinese tallow tree 16 are mixed to produce the tallow base 18, and added to the starter culture vessel 12. The Chinese tallow tree 16 is the *Triadica Sebifera*, which is also referred to as the *Sapium Sebiferum*, or the popcorn tree. The tallow base 18 includes one or more components of the Chinese tallow tree 16 mixed with water 14. It has been found that essentially any part of the Chinese tallow tree 16 can be used in the tallow base 18, including the roots, fruit, leaves, wood, and bark.

It has been found that the use of the tallow base 18 is very effective in adapting micro-organisms 22 to live and thrive in various environments, using different cellulose sources as food sources. The use of trees other than the Chinese tallow tree 16 has not been found to produce the same results, and has been found far less effective in producing micro-organisms 22 adapted to produce ethanol from a wide variety of organic materials 44. The exact reason the Chinese tallow tree 16 is so effective at adapting micro-organisms 22 is not understood at this time. It has been noticed that the micro-organism adaptation process is particularly effective when the sap is running in the Chinese tallow trees 16, such as in the spring and summer seasons, but the adaptation process is still effective with Chinese tallow trees 16 harvested in the fall or winter. There may be compounds present in the sap which are particularly effective for helping to adapt micro-organisms 22 to be more effective in the production of ethanol 50.

There are several characteristics of the Chinese tallow tree 16 which may contribute to the capability of adapting micro-organisms 22. The Chinese tallow tree 16 includes several toxic secondary metabolites in essentially every part of the plant. The toxic compounds present may stress the micro-organisms 22 and aid in the adaptation process, but this is not known for certain. It has been noticed that Chinese tallow trees 16 are very resistant to biological control, such as bacteria, virus, fungi, nematodes, insects and mites, etc. It has been found that many insects are capable of eating the Chinese tallow tree 16, but they do not do so unless all other food sources are exhausted first. The Chinese tallow tree 16 appears to have a wide variety of chemical compounds present, and it has some unusual characteristics. For example, the Chinese tallow tree 16 is very invasive and has become established in some portions of the United States. The Chinese tallow tree 16 tends to quickly pressure out native vegetation, and it grows very fast. The Chinese tallow tree 16 has very high oil content as compared to most trees, and it appears to contain some biologically active compounds.

This description includes a multitude of additives and steps which are used with the starter culture 10, which provide a more robust and effective starter culture 10. It should be noted that the starter culture 10 can be prepared with or without most of the steps listed in this description. Each step provides somewhat of an incremental increase in the effectiveness of the starter culture 10, so the utilization of all the steps provides most robust starter culture 10, but effective starter cultures 10 can be produced using less than all of the steps.

In one embodiment, the tallow base 18 is sterilized with pressure cooking before being inoculated with micro-organisms 22. This sterilization involves pressure cooking the tallow base 18 at a pressure of approximately 16 pounds per square inch gauge for one hour. The sterilization tends to prevent unwanted competition from micro-organisms 22 which are not effective in the fermentation process. However, in some embodiments, it has been found that micro-organisms 22 can be effectively adapted without sterilization of the tallow base 18.

The tallow base 18 can be supplemented with estrogen 20 to improve the starter culture 10. Estrogen 20 can be supplied in various forms. It can be supplied through the addition of female horse urine, and it can also be supplied in tablet form, such as tablets associated with the trademark PREMARIN®. Female horse urine includes other components besides estrogen 20, such as salts and urea, which may play some role in the adaptation of the micro-organisms 22. However, it has been found that the starter culture 10 has comparable quality when prepared estrogen 20 in table form as when it is prepared with female horse urine. When female horse urine is used for the estrogen 20, the female horse urine can be pasteurized or sterilized in advance to reduce inoculation with unwanted micro-organisms 22. Although this does tend to reduce the amount of estrogen 20 present in the female horse urine, there is still enough estrogen 20 left over to be effective in the preparation of the starter culture 10. The estrogen 20 can be added before the micro-organisms 22, or with the micro-organisms 22, or even after the micro-organisms 22, as long as the estrogen 20 is present during the growth stage in the preparation of the starter culture 10.

Starter Culture Inoculation

Micro-organisms 22 are added to the tallow base 18 to inoculate the tallow base 18 and begin the adaptation process. There are several different micro-organisms 22 which can be included in the inoculation stage. One type of micro-organism 22 which is utilized is yeast 24. The yeast 24 can be common baker's yeast 24, *saccharomyces cerevisiae*, but other yeasts 24 can also be used. Certain "super-yeasts," which have been modified in attempts to make them more effective at the production of ethanol 50, have been tried. It has been found that the common baker's yeast 24 or the super-yeast 24 both provide an effective starter culture 10. The use of other yeasts 24 from the genus *saccharomyces* may be effective in the starter culture 10, and the use of yeasts 24 from different genus's may also be effective.

Non pasteurized honey 26 includes a host of micro-organisms 22. When honey is pasteurized, the micro-organisms 22 present are killed, so pasteurized honey does not inoculate the starter culture 10 with the desired micro-organisms 22. The tallow base 18 is inoculated with the non-pasteurized honey 26 such that the micro-organisms present in the non-pasteurized honey 26 are introduced to the starter culture 10. Non-pasteurized honey 26 can come in a variety of forms depending on the type of bee making the honey, the type of pollen being collected, and/or the time of year when the pollen is collected. It has been found that the use of red honey is particularly effective for making a robust starter culture 10. The red honey has been found to be more effective then tupalo honey in providing a micro-organism 22 which improves the starter culture 10. However the use of the tupalo honey does improve the overall effectiveness of the starter culture 10, just not as much as the red honey. Non-pasteurized honey 26 contains a wide variety of micro-organisms 22, and it is not know which micro-organism 22, or which combination of micro-organisms 22, is most effective in the starter culture 10. It is known that the use of non-pasteurized honey 26, and in particular non-pasteurized red honey, is effective for inoculation of the tallow base 18.

Another micro-organism 22 which can be inoculated into the tallow base 18 is the fungus *pichia membranifaciens* 28. It has been found that this particular fungus 28 can be grown on Chinese tallow trees 16 and collected for inoculation into the tallow base 18. The *pichia membranifaciens* fungus 28 has been observed to grow when pieces of the Chinese tallow tree 16 sit in water 14 for extended periods. The *pichia membranifaciens* fungus 28 can then be collected from this tallow base 18 and saved for the starter culture 10. The use of other fungi from the genus *pichia* may also be effective in the preparation of the starter culture 10, as well as fungi from different genus.

Starter Culture Growth Stage

After the tallow base 18 has been created and it has been inoculated with the micro-organisms 22, a growth stage is initiated. In the growth stage, the micro-organisms 22 are allowed to reproduce in the tallow base 18 and adapt to become more effective at producing ethanol 50 from a wide variety of organic compounds. In the growth stage, it has been found that a temperature of approximately 30° C. is effective to keep the micro-organisms 22 active in reproducing and adapting. Controlling the pH of the tallow base 18 below 7 also seems to improve the growth stage for the micro-organisms 22. The Chinese tallow tree 16 tends to have a low pH, and so the use of the Chinese tallow tree 16 in the tallow base 18 is advantageous for controlling the pH of the tallow base 18 below seven.

During the growth stage the tallow base 18 can be oxygenated. A variety of methods can be used, such as mixing of the tallow base 18 or using a bubbler to bubble air up and through the tallow base 18. The presence of oxygen in the growth stage encourages the micro-organisms 22 to grow aerobically, and not to generate significant ethanol 50. Oxygen 30 is present in the air, so a source of oxygen is easy to find for the oxygenation process. The use of oxygen 30 tends to minimize the production of ethanol 50, and ethanol 50 can be toxic to the micro-organisms 22, so it may be the oxygenation primarily serves to control the production of ethanol 50. It is also possible the micro-organisms 22 adapt better because of the oxygen, or the aerobic growth conditions, or some other aspect resulting from the oxygenation of the tallow base 18. Generally, micro-organisms 22 grow faster in aerobic conditions than in anaerobic conditions so it could be that the addition of the oxygen 30 merely speeds the rate of production of an effective starter culture 10 from the inoculated tallow base 18. The exact mechanism by which oxidation of the tallow base 18 improves adaptation of the starter culture 10 is not know, but it is known that oxidation improves the adaptation process.

During the growth stage, the starter culture vessel 12 can be exposed to a magnetic field to increase the adaptation of the micro-organisms 22. It has been found that the use of a negative magnetic field is particularly effective in causing the micro-organisms 22 to adapt. A negative magnetic field is produced by exposing the tallow base 18 to the south pole of a magnet 32, so the south pole of a magnet 32 produces a negative magnetic field, and the north pole of a magnet 32 produces a positive magnetic field. The micro-organisms 22 grow at a faster rate when exposed to a negative magnetic field, and also adapt more quickly.

The growth stage can typically last from two to five days. An observation of the yeast 24 can be used to determine when the starter culture 10 is ready to be used. During the growth stage, the appearance of the yeast 24 changes as the micro-organisms 22 adapt. The yeast becomes larger and more oblong. The growth stage can be carried to the point where the yeast 24 becomes too large and oblong, and are no longer effective in fermentation. In general, the starter culture 10 is ready when the yeast has increased in sized by about 45 to 50 percent and they have become approximately twice as long as they are wide, forming the relatively oblong shape. Observing the change in the yeast serves to indicate when all micro-organisms 22 present in the starter culture 10 are ready, not just when the yeast is ready, so no observations of other types of micro-organisms 22 present are necessary.

Starter Culture Storage and Use

Examining the appearance of the yeast 24 provides a very convenient method for determining when the starter culture 10 is ready for use. When the starter culture 10 is ready for use it can be stored by cooling and maintaining it at a reduced temperature. It has been found that temperatures of approximately 4° C. (centigrade) generally stop any fermentation processes from occurring, but do not kill or deactivate the starter culture 10. Freezing the starter culture 10 can kill and deactivate the micro-organisms 22, so the storage temperature should be controlled above the freezing point. The starter culture 10 can be stored for approximately 4-6 weeks and remain viable. Sometimes the starter culture 10 is so robust that there will be some fermentation at temperatures below 4° C. In such case, the starter culture 10 must be cooled to even lower temperatures nearer the freezing point of the starter culture 10. The starter culture 10 produces carbon dioxide when fermenting, and the carbon dioxide can be seen as bubbles emanating from below the surface of the starter culture 10. One can determine if the starter culture 10 is active by looking to see if any bubbles are being produced below the surface.

After the starter culture 10 has been produced and is used in the fermentation of other organic compounds, such as other sources of cellulosic material, an aliquot of the fermentation mash 40 can be used as the starter culture 10 for subsequent fermentations for a limited period of time. As the mash 40 is re-used as the starter culture 10 in repeated fermentations of organic material 44, the micro-organisms 22 gradually revert back to the state they were in prior to being adapted. Therefore, after a certain number of uses, such as approximately five uses, the organic material 44 to be fermented should be inoculated with a fresh batch of starter culture 10 instead of from a previous fermentation mash 40.

It has been noted that the starter culture 10 described in this description is particularly robust and can thrive on a wide variety of materials. These materials included such things as cellulosic supplies of food, including hardwoods and softwoods. The starter culture 10 seems to most effective when used with soft hardwoods, such as gum trees. Results are also effective on hard hardwoods such as oak trees and on soft woods such as pine trees. The starter culture 10 has been found to be effective for grass clippings, as well as for chicken droppings or chicken guano. The robustness and wide variety of organic compounds which can be fermented using the starter culture 10 of this description provides for a wide variety of uses in industry.

Fermentation

A mash 40 is prepared in a fermentation vessel 42. The mash 40 is typically prepared by adding an organic material 44 to the fermentation vessel 42 with water 14. The organic material 44 can be a wide variety of materials. For example, it can be cellulosic sources, such as trees, including hardwoods, softwoods, soft hardwoods, and hard hardwoods. Trees are typically chipped before fermentation. The average chip size can be approximately 1 centimeter, but a wide variety of chip sizes are possible. The organic material 44 can also be grass clippings, chicken droppings, and it can be a wide variety of other materials. It is anticipated the use of recycled paper and other materials found in common household garbage can be fermented using the starter culture 10. Chinese tallow trees 16 could also be used as the organic material 44, although other cellulosic sources could also be used, including switch grass, straw etc.

The organic material 44 is charged to the fermentation vessel 42, and then exposed to ultrasound prior to beginning the fermentation. The ultrasound can be produced by an ultrasound generation device 34, which can be affixed to the fermentation vessel 42. The ultrasound generation device 34 may also be used on the organic material 44 before the organic material 44 is placed in the fermentation vessel 42. It is also possible the organic material 44 could be exposed to ultrasound during the fermentation, and/or as the fermentation was beginning. Typically, the organic material 44 is exposed to ultrasound before fermentation to limit the exposure of the starter culture 10 to the ultrasound.

The ultrasound tends to loosen up the cellulosic materials and make them more amenable to fermentation. The cellulose can be exposed to the ultrasound until the cellulose begins "fibering," where the structure of the cellulose becomes somewhat fibrous. Different types of cellulose may require exposure to the ultrasound for different periods of time, and tests could be performed on different cellulose sources as needed. Modulating frequencies in the ultrasound can be effective with some materials. Overexposure to the ultrasound does not cause processing problems, and it has been found that varying types of cellulose, such as different types of trees, respond better to different frequencies and intensities of ultrasound. The ultrasound can separate the cellulosic materials of various types of wood to some extent such that the solution in the fermentation vessel 42 is more able to permeate into the cellulosic material. This provides better contact between the organic material 44 and the micro-organisms 22 in the starter culture 10 for fermentation. The starches present in the mash 40 can be measured to determine when the ultrasound process can be terminated.

It has been found that soft hardwoods, such as gum trees, are very amenable to fermentation using the starter culture 10. Hard hardwoods, such as oak, are also very amenable to fermentation, but not as amenable as soft hardwoods. When softwoods such as pine are utilized as the organic material 44, it has been found that exposing the pine wood to ultrasound tends to result in the production of a sap layer on top of the fermentation mash 40. Removal of this sap layer, such as by skimming or filtration, tends to improve the rate at which fermentation proceeds, and may also improve the ethanol yield from the pine wood.

The organic material 44 receives minimal treatment before beginning the fermentation process. The organic material 44 does not have to receive an acid pre-treatment, steam explosion, ammonia expansion, alkaline wet oxidation, or ozone pretreatment. The ultrasound treatment is the primary pre-treatment of the organic material 44, and can be the only pre-treatment in some embodiments. The addition of water 14 and starter culture 10 to the mash 40 are not considered a form of pre-treatment.

Prior to fermentation, the mash 40 is inoculated with an aliquot of the starter culture 10, as is well known in the industry. The mash 40 should not be exposed to micro-organisms 22 which are not included in the starter culture 10 to minimize the change of competing micro-organisms 22 interfering with the fermentation process. As discussed above, an aliquot of a previous mash 40 may be used to inoculate the fermentation vessel 42 with the desired micro-organisms 22, but the micro-organisms 22 tend to gradually revert to their state before being adapted in the starter culture 10. Therefore, the mash 40 should be inoculated with fresh starter culture 10 periodically.

The mash 40 is typically kept at a pH of seven or less, and it has been found that a temperature of approximately 30° C. is conducive to fermentation. Temperatures below 30° C. can slow the rate of fermentation, and temperatures significantly above 30° C. can damage the starter culture 10 and also interfere with fermentation. The fermentation of the mash 40 is performed anerobically. This can be done by filling the fermentation vessel 42 most of the way with the mash 40 and allowing the generation of $CO_2$ (carbon dioxide) to remove air from the air space within the fermentation vessel 42. It would also be possible to inert the fermentation vessel 42, such as with nitrogen or helium, prior to or after the mash 40 is charged to the fermentation vessel 42.

The rate at which the mash produces $CO_2$ can be used to determine when the fermentation is complete. Shortly after the mash 40 is inoculated with the starter culture 10, the rate of $CO_2$ generation is low. As the micro-organism population increases, the rate of $CO_2$ generation increases and the mash 40 begins to bubble more vigorously. As the fermentation process nears completion, the rate of $CO_2$ generation declines. Fermentation can decline based on the available food source for the micro-organisms 22 being depleted, or on the toxicity of the mash 40 increasing due to increased concentrations of ethanol, amongst other reasons. The entire fermentation process typically lasts 3 to 5 days, but this time frame can vary somewhat.

The mash 40 can be exposed to a negative magnetic field within the fermentation vessel 42 during the fermentation process. The use of the negative magnetic field during fermentation tends to speed the fermentation, and may help to improve the ethanol yield from the fermentation. The south pole of magnets 32 are used to produce the negative magnetic field. The use of a non-magnetic fermentation vessel 42 may assist in exposing the mash 40 to a negative magnetic field. A non-metallic fermentation vessel 42 may be used, but some non-magnetic metallic vessels may also be effective.

Many additional factors can be considered for the fermentation process, as known by those skilled in the art. For example, the ethanol 50 produced by the micro-organisms 22 during fermentation can build up to a level where it becomes toxic to the micro-organisms 22. This can result in the termination of the fermentation process. The carbon dioxide generated during the fermentation process is typically vented from the fermentation vessel 42 and simply allowed to escape into the air. It may be desirable to capture any ethanol 50 which may escape with the carbon dioxide by venting this carbon dioxide off gas through a condenser, a scrubber, or some other form of pollution control device. Other fermentation processes known in the art can also be utilized.

Ethanol Recovery

Ethanol 50 is typically recovered from the mash 40 for later use. The recovery of ethanol 50 from the mash 40 involves standard techniques well known in the industry. This can include filtering any remaining organic material 44 from the mash 40, collecting the liquids, distilling the collected liquids to recover the ethanol 50, and separating the ethanol 50 from the water 14. The distillation process typically utilizes a distillation column 52, where ethanol 50 is collected in the overheads, water 14 can be collected from lower points on the distillation column 52, and solids can remain in the reboiler. The distilled ethanol 50 will typically be present as an azeotrope and will still include some water 14. It is also possible to distill the ethanol 50 from the mash 40 without filtering the solids. There are other techniques which may be used to separate the ethanol from the water 14 and from the mash 40, which are known to those skilled in the art. Often times, the water 14 remaining in the ethanol 50 as an azeotrope can be removed before the ethanol 50 is later sold or used. This water 14 can be removed from the azeotrope by passing the azeotrope through an activated carbon bed to absorb the water 14, or by other techniques well known in the industry.

There are generally solids remaining after the fermentation process. The solids can be remaining wood or organic material 44 which was not digested during fermentation, as well as sludge from the micro-organisms 22. These solids can be removed before the ethanol 50 is recovered, or they can be removed afterwards. One way to remove the solids is by filtration. The solids can be disposed of, but other possible uses do exits. For example, it may be possible to compact and dry the solids for use as a fuel, or it may be possible to compost the solids.

EXAMPLE EXPERIMENTS

The process described in this description has been tested, and a wide variety of possible alternatives have been tried. Listed below are some example experiments which demonstrate the results from the various steps described.

TABLE 1

Starter Culture Preparation

| Run | water (oz) | sugar | honey | magnet | estrogen | fungus | yeast | air |
|-----|------|-------|-------|--------|----------|--------|-------|-----|
| 1 | 64 | ½ cup | | 0 | 0 | 0 | SC | no |
| 2 | 64 | ½ cup | | 0 | 0 | 0 | SC | no |
| 3 | 64 | ½ cup | | 0 | 0 | 0 | super | no |
| 4 | 64 | ½ cup | | negative | 0 | PM | super | no |
| 5 | 64 | ½ cup | | positive | 0 | PM | super | no |
| 6 | 64 | 0 | ½ cup tupelo | negative | 0 | PM | super | yes |
| 7 | 64 | 0 | ½ cup tupelo | negative | 4 oz. FHU | PM | super | yes |
| 8 | 64 | 0 | ½ cup tupelo | negative | 2 tablets | PM | super | yes |
| 9 | 64 | 0 | ½ cup red | negative | 2 tablets | PM | super | yes |

All starter cultures included 2.5 lbs of Chinese tallow tree chips. In runs 1-3, the Chinese tallow tree chips remained in solution during the starter culture growth stage. In runs 4-9, the Chinese tallow tree chip solids were pressure cooked and filtered out of the solution before the starter culture inoculation and the starter culture growth stage.
FHU is female horse urine. Estrogen tablets used were those associated with the trademark PREMARIN
PM is pichia membranifaciens.
SC is saccharomyces cerevisiae. Super is a yeast sold which includes saccharomyces cerevisiae, starch, salt, and sorbitan monostearate.

TABLE 2

Fermentation Stage

| Run | cellulose (lbs) | water (gal) | magnet | ultra-sound | starter culture | other | distillate recovered (gal) |
|-----|-----------------|-------------|--------|-------------|-----------------|-------|----------------------------|
| 1 | 2.5 CT | To fill | no | no | all | ground orange | 0.75 |
| 2 | 2.5 CT | to fill | no | no | all | wood not pressure cooked | 0.75 |
| 3 | 2.5 CT | to fill | no | no | all | | |
| 4 | 1.5 MW | 4 | negative | 1 hr | 30 ml | | 0.75 |
| 5 | 1.5 MW | 4 | positive | 1 hr | 30 ml | | 1 |
| 6 | 1.5 MW | 4 | negative | 1 hr | 30 ml | | 1.125 |
| 7 | 1.5 MW | 4 | negative | 1 hr | 30 ml | | 1.25 |
| 8 | 1.5 MW | 4 | negative | 1 hr | 30 ml | | 1.25 |
| 9 | 1.5 MW | 4 | negative | 1 hr | 30 ml | | 1.5 |

CT is Chinese tallow tree. MW is mixed wood, where the wood type can vary. (all runs had 4 lbs of sugar)
Distillate was checked with a burn test, and when the distillate would no longer burn the distillation was stopped. The exact proof of the distillate was not determined.

As can be seen by reviewing Tables 1 and 2, each of several steps incrementally increases the recovery from a set quantity of cellulose.

While the invention has been described with respect to a limited number of embodiments, those skilled in the art, having benefit of this disclosure, will appreciate that other embodiments can be devised which do not depart from the scope of the invention as disclosed here. Accordingly, the scope of the invention should be limited only by the attached claims.

I claim:
1. A method of producing ethanol comprising:
   a) preparing a starter culture, where preparation of the starter culture comprises;
   a1) providing a tallow base comprising Chinese tallow tree parts and water;
   a2) inoculating the tallow base with a microorganism, where the microorganism comprises yeast;
   a3) growing the microorganism in the tallow base in a growth phase;

b) providing a mash, where the mash comprises water and an organic material, and where the organic material is primarily an organic material other than Chinese tallow tree;
c) inoculating the mash with the starter culture;
d) fermenting the mash; and
e) recovering ethanol from the mash.

2. The method of claim 1 where (d) further comprises exposing the mash to a negative magnetic field.

3. The method of claim 2 further comprising exposing the mash to ultrasound before (e).

4. The method of claim 1 where the mash includes softwoods, the method further comprising exposing the mash to ultrasound and recovering sap from the mash before (d).

5. The method of claim 1 where (a2) further comprises adding raw honey.

6. The method of claim 1 where (a2) further comprises adding a fungus from the genus *Pichia*.

7. The method of claim 1 where (a3) further comprises exposing the tallow base to a negative magnetic field.

8. The method of claim 1 further comprising adding estrogen to the tallow base before (a3).

9. The method of claim 1 where (a3) further comprises oxygenating the tallow base.

* * * * *

UNITED STATES PATENT AND TRADEMARK OFFICE
CERTIFICATE OF CORRECTION

PATENT NO. : 8,198,057 B2
APPLICATION NO. : 12/480503
DATED : June 12, 2012
INVENTOR(S) : Randall Padgett It is certified that error appears in the above-identified patent and that said Letters Patent is hereby corrected as shown below:

Title page, item (54) and Column 1, lines 1-3, the title reading "ETHANOL PRODUCTION BY FERMENTATION OF CHINESE TALLOW TREE" should be changed to --CELLULOSIC ETHANOL FERMENTATION USING ADAPTED CULTURE--.

Signed and Sealed this
Seventh Day of August, 2012

David J. Kappos
*Director of the United States Patent and Trademark Office*